(12) United States Patent
Chien et al.

(10) Patent No.: US 12,207,913 B2
(45) Date of Patent: Jan. 28, 2025

(54) SYSTEMS AND METHODS FOR INTRAOPERATIVELY MEASURING ANATOMICAL ORIENTATION

(71) Applicant: DePuy Synthes Products, Inc., Raynham, MA (US)

(72) Inventors: Dennis Chien, West Chester, PA (US); Michael J. O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 332 days.

(21) Appl. No.: 17/851,001

(22) Filed: Jun. 27, 2022

(65) Prior Publication Data

US 2022/0322959 A1   Oct. 13, 2022

Related U.S. Application Data

(63) Continuation of application No. 15/976,482, filed on May 10, 2018, now Pat. No. 11,395,604, which is a
(Continued)

(51) Int. Cl.
*A61B 5/06* (2006.01)
*A61B 5/00* (2006.01)
(Continued)

(52) U.S. Cl.
CPC .............. *A61B 5/06* (2013.01); *A61B 5/067* (2013.01); *A61B 5/1071* (2013.01); *A61B 5/742* (2013.01);
(Continued)

(58) Field of Classification Search
CPC .......... A61B 5/06; A61B 5/067; A61B 5/1071
See application file for complete search history.

(56) References Cited

U.S. PATENT DOCUMENTS 5,156,162 A   10/1992   Gerhardt
5,251,127 A   10/1993   Raab
(Continued)

FOREIGN PATENT DOCUMENTS

CN   101426455 B   11/2011
CN   102694421 B   9/2015
(Continued)

OTHER PUBLICATIONS

U.S. Appl. No. 14/471,120, filed Aug. 28, 2014, Systems and Methods for Intraoperatively Measuring Anatomical Orientation.
(Continued)

*Primary Examiner* — Olivia C Chang
(74) *Attorney, Agent, or Firm* — Barnes & Thornburg LLP

(57) ABSTRACT

Systems and methods are disclosed in which changes in the position and/or orientation of an anatomical structure or of a surgical tool can be measured quantitatively during surgery. In some embodiments, a surgical electronic module can be configured to attach to a surgical device, to continually detect changes in a position and/or orientation of the surgical device during surgery, and to communicate the changes to a user. In this way, where the surgical device is attached to a portion of a patient's anatomy and/or is used to manipulate the patient's anatomy, the surgical electronic module can detect changes in the position and/or orientation of said anatomy. In embodiments where more than one module is used during surgery, the modules can continually detect changes in their positions and/or orientations relative to one another, which correspond to changes in relative positions and/or orientations of the surgical devices to which the modules are attached.

20 Claims, 6 Drawing Sheets

Related U.S. Application Data continuation of application No. 14/471,120, filed on Aug. 28, 2014, now Pat. No. 9,993,177.

(51) Int. Cl.
*A61B 5/107* (2006.01)
*A61B 17/70* (2006.01)
*A61B 34/20* (2016.01)
*A61B 17/90* (2006.01)

(52) U.S. Cl.
CPC .......... *A61B 17/7001* (2013.01); *A61B 34/20* (2016.02); *A61B 5/061* (2013.01); *A61B 17/90* (2021.08); *A61B 2034/2048* (2016.02); *A61B 2034/2053* (2016.02)

(56) References Cited

U.S. PATENT DOCUMENTS

| | | | |
|---|---|---|---|
| 5,291,901 A | 3/1994 | Graf |
| 5,305,203 A | 4/1994 | Raab |
| 5,329,933 A | 7/1994 | Graf |
| 5,748,767 A | 5/1998 | Raab |
| 5,772,610 A | 6/1998 | McGorry et al. |
| 6,015,409 A | 1/2000 | Jackson |
| 6,514,219 B1 | 2/2003 | Guimond et al. |
| 6,565,519 B2 | 5/2003 | Benesh |
| 6,711,432 B1 | 3/2004 | Krause et al. |
| 6,715,213 B2 | 4/2004 | Richter |
| 7,001,346 B2 | 2/2006 | White |
| 7,131,952 B1 | 11/2006 | Dickholtz, Sr. et al. |
| 7,139,601 B2 | 11/2006 | Bucholz et al. |
| 7,335,167 B1 | 2/2008 | Mummy |
| 7,559,931 B2 | 7/2009 | Stone |
| 7,611,522 B2 | 11/2009 | Gorek |
| 7,634,119 B2 | 12/2009 | Tsougarakis et al. |
| 7,634,306 B2 | 12/2009 | Sarin et al. |
| 7,706,000 B2 | 4/2010 | Cohen et al. |
| 7,918,887 B2 | 4/2011 | Roche |
| 7,956,887 B2 | 6/2011 | Hoeg et al. |
| 7,957,809 B2 | 6/2011 | Bourget et al. |
| 7,974,677 B2 | 7/2011 | Mire et al. |
| 7,981,115 B2 | 7/2011 | Justis et al. |
| 8,057,479 B2 | 11/2011 | Stone |
| 8,057,482 B2 | 11/2011 | Stone et al. |
| 8,128,662 B2 | 3/2012 | Altarac et al. |
| 8,167,823 B2 | 5/2012 | Nycz et al. |
| 8,348,954 B2 | 1/2013 | Carls et al. |
| 8,442,621 B2 | 5/2013 | Gorek et al. |
| 8,535,337 B2 | 9/2013 | Chang et al. |
| 8,549,888 B2 | 10/2013 | Isaacs |
| 8,565,853 B2 | 10/2013 | Frigg et al. |
| 8,690,888 B2 | 4/2014 | Stein et al. |
| 8,888,821 B2 | 11/2014 | Rezach et al. |
| 9,198,698 B1 | 12/2015 | Doose et al. |
| 9,554,411 B1 | 1/2017 | Hall et al. |
| 9,579,043 B2 | 2/2017 | Chien et al. |
| 9,993,177 B2 | 6/2018 | Chien et al. |
| 10,335,241 B2 | 7/2019 | Frasier et al. |
| 10,396,606 B2 | 8/2019 | Hall et al. |
| 10,499,996 B2 | 12/2019 | de Almeida Barreto |
| 10,714,987 B2 | 7/2020 | Hall et al. |
| 10,743,944 B2 | 8/2020 | Frasier et al. |
| 10,820,835 B2 | 11/2020 | Gupta et al. |
| 11,089,975 B2 | 8/2021 | Frasier et al. |
| 11,160,619 B2 | 11/2021 | Frasier et al. |
| 11,223,245 B2 | 1/2022 | Hall et al. |
| 11,395,604 B2 | 7/2022 | Chien et al. |
| 11,563,345 B2 | 1/2023 | Hall et al. |
| 2002/0035321 A1 | 3/2002 | Bucholz et al. |
| 2002/0120880 A1 | 8/2002 | Simon et al. |
| 2004/0152970 A1 | 8/2004 | Hunter et al. |
| 2005/0033430 A1 | 2/2005 | Powers et al. |
| 2005/0166410 A1 | 8/2005 | Richter et al. |
| 2005/0222793 A1 | 10/2005 | Lloyd et al. |
| 2005/0251026 A1 | 11/2005 | Stone |
| 2005/0262911 A1 | 12/2005 | Dankowicz et al. |
| 2006/0030771 A1 | 2/2006 | Levine et al. |
| 2006/0100508 A1 | 5/2006 | Morrison |
| 2006/0247773 A1 | 11/2006 | Stamp |
| 2007/0060799 A1 | 3/2007 | Lyon et al. |
| 2007/0106146 A1 | 5/2007 | Altmann et al. |
| 2008/0103557 A1 | 5/2008 | Davis et al. |
| 2008/0177203 A1 | 7/2008 | von Jako |
| 2008/0228195 A1 | 9/2008 | von Jako et al. |
| 2008/0266017 A1 | 10/2008 | Simon et al. |
| 2008/0269767 A1 | 10/2008 | O |
| 2008/0292161 A1 | 11/2008 | Funk et al. |
| 2009/0021752 A1 | 1/2009 | Cohen et al. |
| 2009/0171328 A1 | 7/2009 | Horvath |
| 2009/0249851 A1 | 10/2009 | Isaacs |
| 2010/0010494 A1 | 1/2010 | Quirno |
| 2010/0036384 A1 | 2/2010 | Gorek et al. |
| 2010/0063508 A1 | 3/2010 | Borja et al. |
| 2010/0069919 A1 | 3/2010 | Carls et al. |
| 2010/0087823 A1 | 4/2010 | Kondrashov |
| 2010/0100011 A1 | 4/2010 | Roche |
| 2010/0164296 A1 | 7/2010 | Kurs et al. |
| 2010/0191071 A1 | 7/2010 | Anderson et al. |
| 2010/0191088 A1 | 7/2010 | Anderson et al. |
| 2010/0204575 A1 | 8/2010 | Roche et al. |
| 2010/0204955 A1 | 8/2010 | Roche et al. |
| 2010/0312103 A1 | 12/2010 | Gorek et al. |
| 2011/0040340 A1 | 2/2011 | Miller et al. |
| 2011/0125196 A1 | 5/2011 | Quevedo et al. |
| 2011/0196455 A1 | 8/2011 | Sieracki et al. |
| 2011/0260681 A1 | 10/2011 | Guccione et al. |
| 2011/0270262 A1 | 11/2011 | Justis et al. |
| 2011/0275957 A1 | 11/2011 | Bhandari |
| 2011/0295159 A1 | 12/2011 | Shachar et al. |
| 2012/0035868 A1 | 2/2012 | Roche et al. |
| 2012/0065497 A1 | 3/2012 | Brown et al. |
| 2012/0095330 A1 | 4/2012 | Shechter et al. |
| 2012/0112690 A1 | 5/2012 | Stulen et al. |
| 2012/0123252 A1 | 5/2012 | Brunner |
| 2012/0157019 A1 | 6/2012 | Li |
| 2012/0172653 A1 | 7/2012 | Chornenky et al. |
| 2012/0203140 A1 | 8/2012 | Malchau et al. |
| 2012/0209117 A1 | 8/2012 | Mozes et al. |
| 2012/0232834 A1 | 9/2012 | Roche et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079793 A1 | 3/2013 | Stein et al. |
| 2013/0087950 A1 | 4/2013 | Günther et al. |
| 2013/0131556 A1 | 5/2013 | Chantz |
| 2013/0135312 A1 | 5/2013 | Yang et al. |
| 2013/0165940 A1 | 6/2013 | DiSilvestro |
| 2013/0241468 A1 | 9/2013 | Moshfeghi |
| 2013/0268007 A1 | 10/2013 | Rezach et al. |
| 2013/0303225 A1 | 11/2013 | Maguire |
| 2013/0345718 A1 | 12/2013 | Crawford et al. |
| 2014/0031829 A1 | 1/2014 | Paradis et al. |
| 2014/0052149 A1 | 2/2014 | van der Walt et al. |
| 2014/0057572 A1 | 2/2014 | Klinghult et al. |
| 2014/0088607 A1 | 3/2014 | Recknor |
| 2014/0148808 A1 | 5/2014 | Inkpen et al. |
| 2014/0171965 A1 | 6/2014 | Loh et al. |
| 2014/0200621 A1 | 7/2014 | Malackowski et al. |
| 2014/0232333 A1 | 8/2014 | Kim et al. |
| 2014/0273833 A1 | 9/2014 | McCormack et al. |
| 2014/0273852 A1 | 9/2014 | McCormack et al. |
| 2014/0275940 A1 | 9/2014 | Hladio et al. |
| 2014/0275981 A1 | 9/2014 | Selover et al. |
| 2014/0276871 A1 | 9/2014 | Sherman et al. |
| 2014/0303522 A1 | 10/2014 | Akimoto et al. |
| 2014/0330112 A1 | 11/2014 | Wasielewski |
| 2015/0011874 A1 | 1/2015 | Amoako-Tuffour et al. |
| 2015/0057733 A1 | 2/2015 | Lotfi |
| 2015/0137746 A1 | 5/2015 | Lee et al. |
| 2015/0142372 A1 | 5/2015 | Singh |
| 2015/0150646 A1 | 6/2015 | Pryor et al. |
| 2015/0180263 A1 | 6/2015 | Sud et al. |
| 2015/0185846 A1 | 7/2015 | Otto et al. |

(56) References Cited

U.S. PATENT DOCUMENTS

| | | |
|---|---|---|
| 2015/0272694 A1 | 10/2015 | Charles |
| 2015/0305786 A1 | 10/2015 | Wehrle et al. |
| 2015/0313482 A1 | 11/2015 | Nabutovsky et al. |
| 2015/0313566 A1 | 11/2015 | Diers et al. |
| 2016/0007909 A1 | 1/2016 | Singh et al. |
| 2016/0022176 A1* | 1/2016 | Le Huec ............... A61B 6/461 600/594 |
| 2016/0058320 A1 | 3/2016 | Chien et al. |
| 2016/0058523 A1 | 3/2016 | Chien et al. |
| 2016/0191887 A1 | 6/2016 | Casas |
| 2016/0225192 A1 | 8/2016 | Jones et al. |
| 2016/0235480 A1 | 8/2016 | Scholl et al. |
| 2016/0262800 A1 | 9/2016 | Scholl et al. |
| 2016/0360997 A1 | 12/2016 | Yadav et al. |
| 2017/0143426 A1 | 5/2017 | Isaacs et al. |
| 2017/0189121 A1 | 7/2017 | Frasier et al. |
| 2017/0194820 A1 | 7/2017 | Hall et al. |
| 2017/0196507 A1 | 7/2017 | Singh et al. |
| 2017/0224425 A1 | 8/2017 | Lee et al. |
| 2017/0231709 A1 | 8/2017 | Gupta et al. |
| 2017/0348061 A1 | 12/2017 | Joshi et al. |
| 2018/0070860 A1 | 3/2018 | Gupta et al. |
| 2018/0256067 A1 | 9/2018 | Chien et al. |
| 2018/0279913 A1 | 10/2018 | Frasier et al. |
| 2019/0090955 A1 | 3/2019 | Singh et al. |
| 2019/0321109 A1 | 10/2019 | Frasier et al. |
| 2019/0341818 A1 | 11/2019 | Hall et al. |
| 2020/0297432 A1 | 9/2020 | Frasier et al. |
| 2020/0303971 A1 | 9/2020 | Hall et al. |
| 2021/0059563 A1 | 3/2021 | Gupta et al. |
| 2021/0338107 A1 | 11/2021 | Frasier et al. |
| 2022/0039877 A1 | 2/2022 | Frasier et al. |
| 2022/0103024 A1 | 3/2022 | Hall et al. |

FOREIGN PATENT DOCUMENTS

| | | |
|---|---|---|
| CN | 103385708 B | 9/2015 |
| CN | 103748763 B | 3/2016 |
| CN | 105378820 B | 2/2018 |
| CN | 104854533 B | 1/2019 |
| CN | 105011977 B | 2/2020 |
| EP | 1943954 B1 | 5/2011 |
| EP | 2901957 A1 | 8/2015 |
| EP | 2597783 B1 | 1/2018 |
| GB | 190927693 A | 9/1910 |
| JP | 2000254141 A | 9/2000 |
| JP | 2003523795 A | 8/2003 |
| JP | 2005095433 A | 4/2005 |
| JP | 3746628 B2 | 2/2006 |
| JP | 4323276 B2 | 9/2009 |
| JP | 2009273521 A | 11/2009 |
| JP | 2010233354 A | 10/2010 |
| JP | 2012120648 A | 6/2012 |
| JP | 2013544144 A | 12/2013 |
| JP | 2015502766 A | 1/2015 |
| JP | 2015109785 A | 6/2015 |
| JP | 2015213753 A | 12/2015 |
| JP | 2017510307 A | 4/2017 |
| WO | 1991003980 A1 | 4/1991 |
| WO | 1999015097 A2 | 4/1999 |
| WO | 2005077000 A2 | 8/2005 |
| WO | 2013053398 A1 | 4/2013 |
| WO | 2013169674 A1 | 11/2013 |
| WO | 2014025305 A1 | 2/2014 |
| WO | 2014063181 A1 | 5/2014 |
| WO | 2015003224 A1 | 1/2015 |
| WO | 2015114119 A1 | 8/2015 |
| WO | 2015162965 A1 | 10/2015 |
| WO | 2016032875 A1 | 3/2016 |
| WO | 2019055912 A1 | 3/2019 |

OTHER PUBLICATIONS

U.S. Appl. No. 14/934,237, filed Nov. 6, 2015, Systems and Methods for Intraoperatively Measuring Anatomical Orientation.
U.S. Appl. No. 14/983,818, filed Dec. 30, 2015, Systems and Methods for Intraoperatively Measuring Anatomical Orientation.
U.S. Appl. No. 14/983,828, filed Dec. 30, 2015, Systems and Methods for Wirelessly Powering or Communicating With Sterile-Packed Devices.
U.S. Appl. No. 15/263,023, filed Sep. 12, 2016, Systems and Methods for Anatomical Alignment.
U.S. Appl. No. 15/375,307, filed Dec. 12, 2016, Systems and Methods for Wirelessly Powering or Communicating With Sterile-Packed Devices.
U.S. Appl. No. 15/429,566, filed Feb. 20, 2017, Systems and Methods for Intraoperatively Measuring Anatomical Orientation.
U.S. Appl. No. 15/475,587, filed Mar. 31, 2017, Systems, Devices and Methods for Enhancing Operative Accuracy Using Inertial Measurement Units.
U.S. Appl. No. 15/976,482, filed May 10, 2018, Systems and Methods for Intraoperatively Measuring Anatomical Orientation.
U.S. Appl. No. 16/434,166, filed Jun. 6, 2019, Method and Apparatus for Intraoperative Measurements of Anatomical Orientation.
U.S. Appl. No. 16/515,005, filed Jul. 17, 2019, Systems and Methods for Wirelessly Powering or Communicating With Sterile-Packed Devices.
U.S. Appl. No. 16/892,955, filed Jun. 4, 2020, Method and Apparatus for Intraoperative Measurements of Anatomical Orientation.
U.S. Appl. No. 16/894,245, filed Jun. 5, 2020, Systems and Methods for Wirelessly Powering or Communicating With Sterile-Packed Devices.
U.S. Appl. No. 17/066,472, filed Oct. 8, 2020, Systems and Methods for Anatomical Alignment.
U.S. Appl. No. 17/378,639, filed Jul. 16, 2021, Systems, Devices and Methods for Enhancing Operative Accuracy Using Inertial Measurement Units.
U.S. Appl. No. 17/509,665, filed Oct. 25, 2021, Method and Apparatus for Intraoperative Measurements of Anatomical Orientation.
U.S. Appl. No. 17/545,839, filed Dec. 8, 2021, Systems and Methods for Wirelessly Powering or Communicating With Sterile-Packed Devices.
Baka, Nora, et al. "2D-3D shape reconstruction of the distal femur from stereo X-ray imaging using statistical shape models," Medical image analysis 15.6 (2011): 840-850.
Conn, K. S., M. T. Clarke, and J.P. Hallett, "A Simple Guide to Determine the Magnification of Radiographs and to Improve the Accuracy of Preoperative Templating," Bone & Joint Journal 84.2 (2002): 269-272.
Delorme, et al., Intraoperative comparison of two instrumentation techniques for the correction of adolescent idiopathic scoliosis. Rod rotation and translation. Spine (Phila Pa 1976). Oct. 1, 1999;24(19):2011-7.
Extended European Search Report for Application No. 17849374.8, dated Mar. 31, 2020 (8 pages).
Ghanem, et al., Intraoperative optoelectronic analysis of three-dimensional vertebral displacement after Cotrel-Dubousset rod rotation. A preliminary report. Spine (Phila Pa 1976). Aug. 15, 1997:22(16):1913-21.
Gorski, J.M., and Schwartz, L. "A Device to Measure X-ray Magnification in Preoperative Planning for Cementless Arthroplasty," Clinical Orthopaedics and Related Research 202 (1986): 302-306.
Australian Office Action for Application No. 2016380934, issued Sep. 16, 2020 (6 pages).
Australian Office Action for Application No. 2016380934, issued Feb. 5, 2021, (5 pages).
Chinese Office Action for Application No. 201680077321.9, issued Jan. 6, 2021 (17 pages).
Chinese Supplemental Search Report for Application No. 201680077321.9, issued Dec. 5, 2021 (1 page).
Chinese Office Action for Application No. 201780055976.0, issued Mar. 24, 2021 (22 pages).
Chinese Supplemental Search Report for Application No. 201780055976.0, issued Nov. 20, 2021 (1 page).
International Search Report and Written Opinion for Application No. PCT/US2015/046217, mailed Nov. 9, 2015 (11 pages).

(56) References Cited

OTHER PUBLICATIONS

International Search Report and Written Opinion for Application No. PCT/US2016/067134, mailed Sep. 11, 2017 (20 pages).
International Search Report and Written Opinion for Application No. PCT/US2016/067140, mailed Mar. 23, 2017 (13 pages).
International Search Report and Written Opinion for Application No. PCT/US2017/017344, mailed Jul. 13, 2017 (22 pages).
International Search Report for Application No. PCT/US2017/050023, mailed Jan. 8, 2018 (6 Pages).
International Search Report and Written Opinion for Application No. PCT/US2018/024791, mailed Aug. 6, 2018 (12 pages).
Invitation to Pay Additional Fees for Application No. PCT/US2016/067134, mailed Jun. 26, 2017 (14 pages).
Japanese Office Action for Application No. 2018-534634, mailed Nov. 10, 2020 (12 pages).
Japanese Office Action for Application No. 2019-513849, mailed Jun. 8, 2021 (6 pages).
Japanese Office Action for Application No. 2019-553503, mailed Dec. 14, 2021 (10 pages).
King, R. J., et al. "A Novel Method of Accurately Calculating the Radiological Magnification of the Hip," Bone & Joint Journal 91.9 (2009): 1217-1222.
Lafon, et al., Intraoperative three dimensional correction during in situ contouring surgery by using a numerical model. Spine (Phila Pa 1976). Feb. 15, 2010;35(4):453-9. doi: 10.1097/BRS.0b013e3181b8eaca. Abstract.
Lafon, et al., Intraoperative three-dimensional correction during rod rotation technique. Spine (Phila Pa 1976). Mar. 1, 2009;34(5):512-9. doi: 10.1097/BRS.0b013e31819413ec.
Lamecker, Hans, Thomas H. Wenckebach, and H-C. Hege. "Atlas-based 3D-shape reconstruction from X-ray images," Pattern Recognition, 2006. ICPR 2006. 18th International Conference on. vol. 1. IEEE, 2006; pp. 1-4.
Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.
Mac-Thiong, et al., A new technique for intraoperative analysis of trunk geometry in adolescent idiopathic scoliosis. Can J Surg. Jun. 2002;45(3):219-23.
Mac-Thiong, et al., The effect of intraoperative traction during posterior spinal instrumentation and fusion for adolescent idiopathic scoliosis. Spine (Phila Pa 1976). Jul. 15, 2004;29(14):1549-54.
Markelj, Primoz, et al. "A review of 3D/2D registration methods for image-guided interventions," Medical Image analysis 16.3 (2012): 642-661.
Mazzilli, F., et al. "Ultrasound Energy Harvesting System for Deep Implanted-Medical-Devices (IMDs)", 2012 IEEE International Symposium on Circuits and Systems (ISCAS), Seoul, 2012, pp. 2865-2868.
Sarkalkan, Nazli, Harrie Weinans, and Amir A. Zadpoor, "Statistical shape and appearance models of bones," Bone 60 (2014): 129-140.
Schumann, S., Thelen, B., Ballestra, S., Nolte, L. P., Buchler, P., & Zheng, G., "X-ray Image Calibration and Its Application to Clinical Orthopedics," Medical Engineering & Physics (2014): 36(7), 968-974.
The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589.
Written Opinion for Application No. PCT/US2017/050023, mailed Jan. 8, 2018 (4 Pages).
Zheng, Guoyan, et al., "A 2D/3D correspondence building method for reconstruction of a patient-specific 3D bone surface model using point distribution models and calibrated X-ray images," Medical image analysis 13.6 (2009): 883-899.

* cited by examiner

SYSTEMS AND METHODS FOR INTRAOPERATIVELY MEASURING ANATOMICAL ORIENTATION

CROSS-REFERENCE TO RELATED APPLICATIONS

This application is a continuation of U.S. patent application Ser. No. 15/976,482, filed May 10, 2018, entitled "Systems and Methods for Intraoperatively Measuring Anatomical Orientation." U.S. patent application Ser. No. 15/976,482 is a continuation of U.S. patent application Ser. No. 14/471,120, filed Aug. 28, 2014, entitled "Systems and Methods for Intraoperatively Measuring Anatomical Orientation," now issued as U.S. Pat. No. 9,993,177. Each of these applications is hereby incorporated by reference in its entirety.

FIELD

The present disclosure is related to systems and methods for measuring anatomical position and/or orientation. In some embodiments, systems and methods quantitatively measure changes in the position and/or orientation of a portion of a patient's anatomy with respect to another portion of the patient's anatomy during surgery.

BACKGROUND

Many surgical procedures require a surgeon to intraoperatively assess changes in the position or orientation of one or more portions of a patient's anatomy. However, even in open surgeries, there can be obstructions that prevent a surgeon from viewing relevant anatomy at a surgical site, e.g., blood, adjacent soft tissue, etc. Traditional surgical procedures use imaging techniques, such as CT-scans, x-rays, etc., to pre-operatively plan for a desired anatomical correction and then to post-operatively assess whether the desired anatomical correction has been achieved. Viewing the anatomical changes intraoperatively using such imaging techniques can be difficult, however, as it may require interruption of the surgery. Also, many imaging techniques only provide snapshots illustrating progressive changes in a qualitative manner, but do not provide data of changes as they occur in real-time. A further limitation of such imaging techniques is that they may only provide qualitative data, thus requiring a surgeon to make a subjective assessment of when a desired anatomical orientation has been achieved. Such imaging techniques also expose the patient and the operating room staff to potentially-harmful radiation.

During a traditional pedicle subtraction osteotomy, surgeons remove bone from a vertebra of a patient suffering from a spinal deformity to correct spinal curvature. To intraoperatively determine when the appropriate amount of bone has been removed, the surgeon must be able to accurately assess the amount of correction that has been achieved at a given time. Traditionally, to make this assessment, the surgeon must step back from the surgical procedure while an imaging device is brought in and positioned to view the curvature of the spine. However, this provides only a subjective measure of angular correction and involves an interruption in the surgical procedure, adding time and inconvenience. Often times, this results in sub-optimal patient outcomes and repeat surgeries due to over- or under-correction of the deformity.

Thus, there is a need for improved systems and methods for intraoperatively measuring anatomical position and/or orientation.

SUMMARY

Systems and methods are disclosed in which changes in the position and/or orientation of an anatomical structure or of a surgical tool can be measured quantitatively during surgery. In some embodiments, a surgical electronic module can be configured to attach to a portion of a patient's anatomy and/or to a surgical device, to continually detect changes in a position and/or orientation of the patient's anatomy and/or the surgical device during surgery, and to communicate the changes to a user. Where the surgical device is attached to a portion of a patient's anatomy and/or is used to manipulate the patient's anatomy, the surgical electronic module can detect changes in the position and/or orientation of said anatomy. In embodiments where more than one module is used during surgery, the modules can continually detect changes in their positions and/or orientations relative to one another, which correspond to changes in relative positions and/or orientations of portions of the patient's anatomy and/or the surgical devices to which the modules are attached.

In one exemplary embodiment, a surgical electronic module is provided that includes a housing having one or more engagement features that are configured to removably attach the housing to a surgical device, a sensor, a processor, and a display. The sensor can be disposed in the housing and can be configured to detect a position or orientation of the module with respect to the earth. The processor can be coupled to the sensor and can be configured to calculate a change in position or orientation of the surgical device with respect to one or more reference points when the surgical device is attached to the module, based on the position or orientation detected by the sensor. The display can be configured to display the change calculated by the processor to thereby assist a user in assessing changes in position or orientation of anatomy coupled to or manipulated by the surgical device. In some embodiments, the display can be disposed on the housing.

In some embodiments, the surgical electronic module can include additional components. By way of non-limiting example, the surgical electronic module can further include a reset mechanism that, when actuated, sets an initial position or orientation of the module to be used in calculating the change in the position or orientation of the surgical device. Additionally or alternatively, the surgical electronic module can include a memory configured to store at least one of the position or orientation detected by the sensor and the change calculated by the processor. In still further embodiments, the surgical electronic module can include a communications interface configured to send the position or orientation detected by the sensor to an external device and to receive a position or orientation of the one or more reference points from the external device. The external device can be a second surgical electronic module.

In some embodiments, the one or more reference points can include a second surgical electronic module. In some embodiments, the sensor can be configured to detect the position or orientation at predetermined time intervals and/or the processor can be configured to calculate the change at the predetermined time intervals. The processor can further be configured to calculate first, second, and/or third derivatives of the position or orientation of the surgical device. In still further embodiments, the one or more engagement features can be configured to identify an aspect of the surgical device when the surgical device is attached to the module.

In another aspect, a surgical method is provided for measuring a change in anatomical position or orientation. The method can involve detecting an absolute angle of a first electronic module attached to a first surgical device by a sensor of the first electronic module, with the first surgical device being operatively coupled with a first portion of a patient's anatomy and detecting an absolute angle of a second electronic module attached to a second surgical device by a sensor of the second electronic module, with the second surgical device being operatively coupled with a second portion of the patient's anatomy. The method can also include calculating by a processor of at least one of the first and second electronic modules a change in an angle of the first electronic module with respect to the second electronic module multiple times during a surgery to determine a change in an angle of the first surgical device with respect to the second surgical device. The method can further include conveying to a user the change in the angle of the first surgical device with respect to the second surgical device to thereby assist the user in determining a change in an angle of the first portion of the patient's anatomy with respect to the second portion of the patient's anatomy. In some embodiments, the change in the angle of the first surgical device with respect to the second surgical device is conveyed to the user on a display of at least one of the first electronic module and the second electronic module.

In some embodiments, the method can further include actuating reset mechanisms of the first and second electronic modules to set an initial angle of the first module with respect to the second module. The initial angle can be used in calculating the change in the angle of the modules relative to one another. The calculating and the conveying steps can be repeated until a target position or orientation of the first surgical device with respect to the second surgical device has been reached. In such embodiments, the method can further include alerting the user when the target position or orientation has been reached. In still further embodiments, the method can include calculating a rate of the change in the angle of the first surgical device with respect to the second surgical device.

In some embodiments, the first and second portions of the patient's anatomy are first and second vertebra on opposite sides of an osteotomy site. When the first portion of the patient's anatomy is a first vertebra and the first surgical device is a first bone screw implanted in the first vertebra, the method can further include attaching the first electronic module to the first bone screw. Additionally, when the second portion of the patient's anatomy is a second vertebra disposed opposite an osteotomy site from the first vertebra and the second surgical device is a second bone screw implanted in the second vertebra, the method can further include attaching the second electronic module to the second bone screw. In such embodiments, the method can also include locking a spinal rod to the first and second bone screws after a target position or orientation of the first vertebra with respect to the second vertebra has been reached.

In yet another aspect, a surgical method is provided for guiding a surgical instrument. The method can include detecting an orientation of a first electronic module that is attached to the surgical instrument by a sensor of the first electronic module, detecting a position of the first electronic module via communications between the first electronic module and at least two electronic modules attached to at least two surgical devices, calculating by a processor of the first electronic module a change in the orientation of the surgical instrument and a change in the position of the surgical instrument over time, and conveying to a user the change in the orientation and the position of the surgical instrument to thereby assist the user in guiding the surgical instrument during surgery. In some embodiments, the change in the position and the orientation of the surgical instrument is conveyed to the user on a display of the first electronic module. In some embodiments, the at least two surgical devices do not move with respect to a patient's anatomy while the user is guiding the surgical instrument.

The present invention further provides devices and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
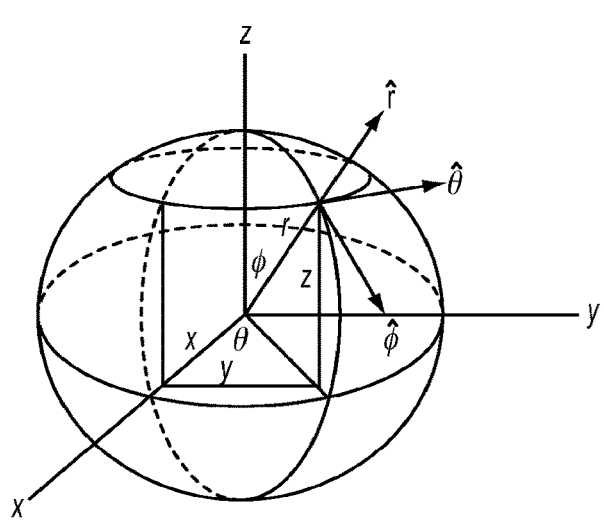
FIG. 1A is a schematic illustration of a spherical coordinate system.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale.

Systems and methods are disclosed in which changes in a position and/or orientation of an anatomical structure or of a surgical tool can be measured quantitatively during surgery. In some embodiments, a surgical electronic module can be configured to attach to a surgical device, to continually detect changes in a position and/or orientation of the surgical device during surgery, and to communicate the changes to a user. In this way, where the surgical device is attached to a portion of a patient's anatomy and/or is used to manipulate the patient's anatomy, the surgical electronic module can detect changes in the position and/or orientation of said anatomy. In embodiments where more than one module is used during surgery, the modules can continually detect changes in their positions and/or orientations relative to one another, which correspond to changes in relative positions and/or orientations of the surgical devices to which the modules are attached. Additionally or alternatively, at least one of the modules can help to establish a reference 3D location in the operating room, particularly where the at least one of the modules is stationary. In some embodiments, the modules can include a resetting or "zeroing" function that allows a user to selectively set an initial relative position and/or orientation of the modules to zero. Subsequent changes in the relative positions and/or orientations of the modules can then be measured and displayed to the user so that the user knows when a desired change in position and/or orientation of the modules has been reached. In some embodiments, all of the components necessary for detecting, calculating, and/or communicating positional information (i.e., position and/or orientation) are contained within the module itself, thus eliminating the need for an external base station or other additional bulky equipment. By thus providing a means for quantitatively measuring changes in anatomical orientation in real-time during surgery, exemplary systems and methods provided herein can enhance the accuracy of the surgery and reduce or eliminate the need for intraoperative imaging, thereby reducing radiation exposure and increasing efficiency.

The positional information detected and/or calculated by the surgical electronic module can include one or more angles of the module with respect to the earth (referred to hereinafter as "absolute" angles), one or more angles of the module with respect to a some other reference point (referred to hereinafter as "relative" angles), distances between the module and one or more external reference points, changes in any of these values, a rate of changes in any of these values, and/or higher order derivatives of any of these values. The module can be configured to detect and/or calculate the positional information in a variety of units and coordinate systems.

Figure 1B:
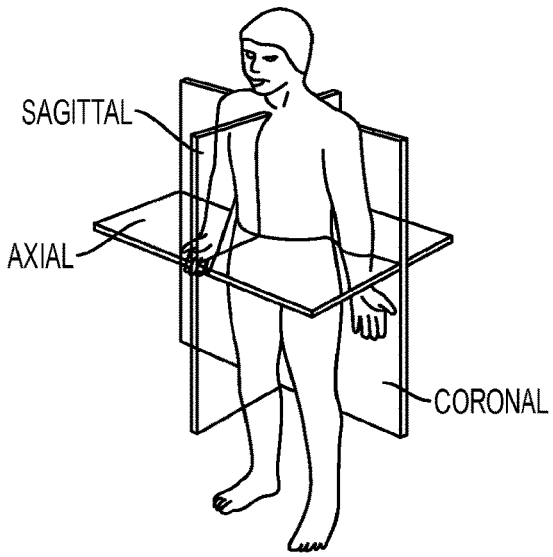
FIG. 1B is a schematic illustration of relevant anatomical planes.

To provide relevant anatomical measurements during surgery, in some embodiments the module can be configured to translate positions and/or orientations detected in a spherical coordinate system, illustrated in FIG. 1A and defined by an absolute azimuth angle $\theta$, an absolute polar angle $\varphi$, and a radial distance r, into positions and/or orientations along the sagittal, axial, and coronal planes, illustrated in FIG. 1B.

Figure 2:
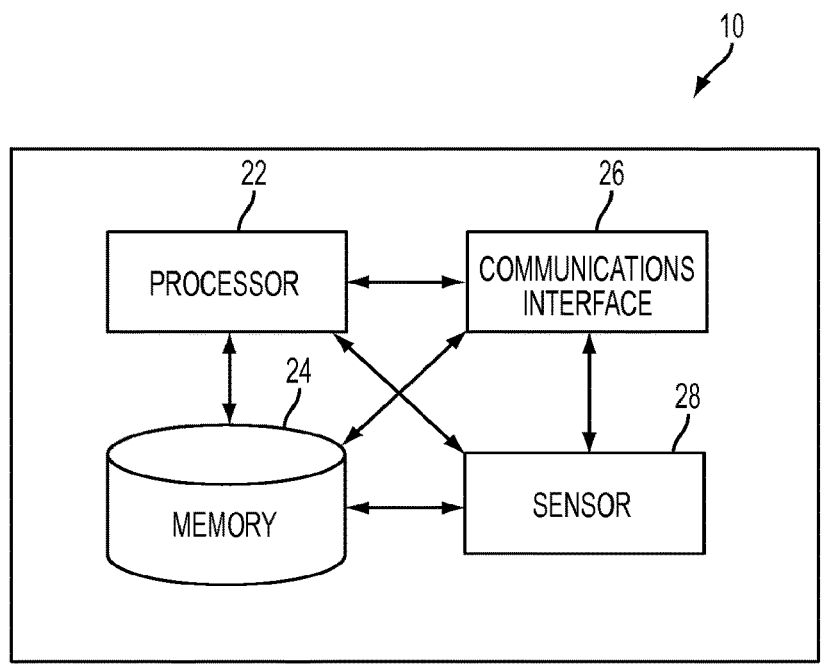
FIG. 2 is a schematic illustration of an exemplary surgical electronic module.

The surgical electronic module can include one or more components for detecting, processing, communicating, and/or storing positional information of the module and the surgical device to which it is attached. As schematically illustrated in FIG. 2, an exemplary module 10 can include a processor 22, a memory 24, a communications interface 26, and a sensor 28—all of which can be in communication with each other. Any of these components can exist external to the module 10, however, for example at a remote base station configured to communicate with the module 10 through the communications interface 26. Further, although each of these components are referred to in the singular, it will be appreciated by a person skilled in the art that the various functions described as being carried out by one of the components can actually be carried out by multiple of those components, e.g., the functions described as being carried out by the processor 22 can be carried out by multiple processors. The electrical components can be powered by a battery contained within the module 10, for example a lithium ion battery, or can be powered by an external power source coupled to the module 10 via an adaptor.

The sensor 28 can be or can include any type of sensor that is configured to detect positional information of the module 10. By way of non-limiting example, the sensor 28 can include an accelerometer (e.g., a 9-axis accelerometer for measuring one or more angles of the module 10 with respect to a reference point such as the earth), a gyroscopic sensor, a geomagnetic sensor, and the like. Additionally or alternatively, where the module 10 is configured to detect a distance of the module from a reference point, the sensor 28 can include ultrasound, electromagnetic, and/or infrared transceivers for communicating with a positioning system. In an exemplary embodiment, the sensor 28 can be configured to detect an absolute position and/or orientation of the module in the spherical coordinate system. The sensor 28 can be configured to detect the positional information at intervals throughout a surgical procedure, for example every second, every millisecond, every microsecond, etc., such that the positional information is effectively detected continuously and in real-time. The positional information can be detected regularly, intermittently, or at non-regular intervals. The positional information can be conveyed to the surgeon, stored in the memory 24, conveyed to the processor 22 for processing, and/or communicated to one or more external devices via the communications interface 26 for processing or storage.

Where the sensor 28 is configured to detect both an orientation and a position (e.g., a distance of the module 10 from some reference point), the module 10 can be configured to switch between an orientation detection mode in which the sensor 28 detects only the orientation and a full detection mode in which the sensor 28 detects both the orientation and the position. The module 10 can be configured to switch between the orientation detection mode and the full detection mode at the request of the surgeon, for example via actuation of an input device on the module 10, and/or based on an identity of the surgical device to which the module 10 is attached.

The processor 22 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 22 can be configured to generate positional information and/or perform various calculations based on the positional information detected by the sensor 28, stored in the memory 24, and/or received from an external device via the communications interface 26. By way of non-limiting example, the processor 22 can be configured to calculate a relative position and/or orientation of the module 10 with respect to an external reference point based on an absolute position and/or orientation of the module 10 that is detected by the sensor 28 and/or an absolute position and/or orientation of the external reference point that is received through the communications interface 26. The processor 22 can be configured to calculate changes in the absolute and relative positions and/or orientations of the module 10 and/or a speed at which those changes occur, which will correspond to changes and/or a speed of the surgical device to which the module 10 is attached.

The processor 22 can be coupled to the memory 24, which can include a random access memory (RAM), a read-only memory (ROM), a flash memory, a non-transitory computer readable storage medium, and so forth. The memory 24 can store instructions for execution by the processor 22 to implement the systems disclosed herein or to execute the methods disclosed herein. Additionally or alternatively, the memory 24 can store the positional information sensed by the sensor 28, calculated by the processor 22, and/or received from an external device through the communications interface 26.

The communications interface 26 can be configured to receive and transmit information from any of the processor 22, the memory 24, and the sensor 28 with one or more external devices, e.g., another surgical electronic module, a base station, etc. The communications interface 26 be wireless (e.g., near-field communication (NFC), Wi-Fi, Bluetooth, Bluetooth LE, ZigBee, and the like) or wired (e.g., USB or Ethernet). In the case of NFC, for example, the module 10 can include a radio transceiver configured to communicate with a radio transceiver of another device, e.g., a second module, using one or more standards such as ISO/IEC 14443, FeliCa, ISO/IEC 18092, and those defined by the NFC Forum. The communication interface 26 can be selected to provide the desired communication range. In some embodiments, Bluetooth (e.g., class 2 Bluetooth having a range of 5-10 meters) can be used for the communication interface to allow the module 10 to remain somewhat distant from the device with which it is communicating, e.g., the second module and/or a base station, while at the same time limiting the communication range such that other mobile devices unlikely to be used in the surgery are not needlessly involved.

Figure 3:
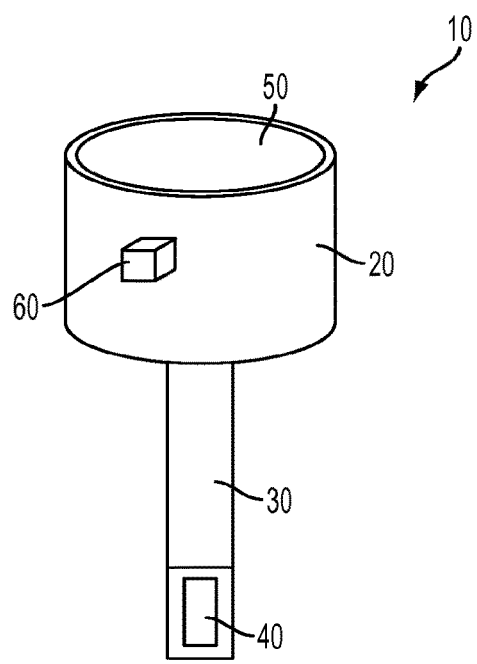
FIG. 3 is a perspective view of the surgical electronic module of FIG. 2.

As shown in FIG. 3, the exemplary module 10 can include a proximal housing 20 and a distal shaft 30. In general, the housing 20 and the shaft 30 can be any size and shape configured to be inserted at least partially into a patient's body during surgery while not substantially obstructing a surgeon's view of or access to a surgical site. Any or all of the above described components for detecting, processing, and/or communicating positional information can be housed within the housing 20. Further, the housing 20 can have various external features for inputting and outputting the positional information, for example the housing 20 can include an electronic display 50 for communicating information detected and/or calculated by the module 10 and/or a zeroing button 60 to allow the user to indicate that the module 10 is in an initial position and/or orientation. The shaft 30 can extend distally from the housing 20 and can be configured to rigidly and mechanically attach the module 10 to the surgical device such that changes in the position and/or orientation of the surgical device result in corresponding changes in the position and/or orientation of the module 10.

The display 50 can be configured to communicate the positional information detected and/or calculated by the module 10 to assist the surgeon in assessing anatomical changes effected by the surgical device to which the module 10 is attached. In the illustrated embodiment, the display 50 is formed on a proximal-facing surface of the housing 20, although the display 50 can be located anywhere on the module 10, e.g., such that it is visible to the surgeon during surgery, or it can be located remotely from the module. The display 50 can be any type of display screen, e.g., liquid crystal, light emitting diode, etc., and in some embodiments can be configured to withstand exposure to sterilization, liquids, and/or high levels of moisture. In an exemplary embodiment, the display 50 can display a change in the absolute or relative position and/or orientation of the module 10 during surgery, which corresponds to a change in the position and/or orientation of the surgical device to which the module 10 is attached. In some embodiments, the display 50 can additionally or alternatively provide positive and/or negative feedback to the surgeon about the position and/or orientation of the module 10. By way of non-limiting example, when the module 10 detects that a desired position and/or orientation has been reached, the display 50 can provide positive feedback to the surgeon, e.g., a green light. When the module 10 is determined to be outside a desirable positional range, the display 50 can provide negative feedback to the surgeon, e.g., a red light, an error message, etc. Other means for communicating information to the surgeon can include, without limitation, a vibrator, a speaker or buzzer for providing audio feedback and an internal or external display in communication with the module 10 for providing visual feedback. The external display can be larger than the display 50 and, in some embodiments, can provide a real-time graphical illustration of the movement of the module 10 and optionally one or more other modules during surgery.

The positional information output by the module 10, for example on the display 50, can be reset to zero at any time by user actuation of a resetting or "zeroing" mechanism to thereby indicate that the module 10 is in an initial position and/or orientation. For example, a position and/or orientation of the module 10 displayed at a starting point of the surgery can to be set to zero upon actuation of the zeroing button 60 by the surgeon, although it will be appreciated by a person skilled in the art that the zeroing mechanism can be any feature on the module 10 or it can be remote to the module 10. After the zeroing button 60 has been pressed, the display 50 can display a change in the position and/or orientation of the module 10 relative to a zero position and/or orientation, such that the surgeon can readily know the difference between the initial position and/or orientation of the module 10 and a current position and/or orientation of the module 10. Thus, where the surgery requires changing a position and/or orientation of a patient's anatomy that is connected to the module 10 via the surgical device by a desired amount, the surgeon can know that the desired change has been effected when the desired change of the module 10 is displayed on the display 50. In some embodiments, actuation of the button 60 can also initiate detection and/or calculation of the position and/or orientation of the module 10.

The module 10 can be configured to attach directly to a patient's anatomy and/or to the surgical device via one or more engagement features 40 formed on a distal portion of the module 10, for example on the distal end of the shaft 30. The surgical device can be anything used in the operating room that facilitates the surgery, including, by way of non-limiting example, surgical implants, surgical instruments, fixtures in the operating room, e.g., an operating table, etc. The engagement features 40 can be specifically configured to mate the module 10 only to a single type of surgical device, or they can be adaptable or modular to allow for mating of the module 10 to any of a variety of surgical devices. Further, the engagement features 40 can be configured to mate the module 10 to more than one surgical device at a time. The engagement features 40 can provide for direct rigid mechanical attachment of the module 10 to the surgical device to thereby ensure that changes in a position and/or orientation of the surgical device result in corresponding changes in the position and/or orientation of the module 10. In some embodiments, the engagement features 40 can be configured to rigidly attach to engagement features of another surgical electronic module to calibrate the module 10 with the other surgical electronic module, e.g., by synchronizing coordinate systems. Non-limiting examples of engagement features 40 include a snap mechanism, a lock-and-key mechanism, an electronic contact, a screw or other threaded feature, etc.

In some embodiments, the engagement features 40 can be configured to detect identification information about the surgical device to which the module 10 is attached. For example, the engagement features 40 can comprise one or more buttons, switches, pressure transducers, etc. that are configured to align with one or more protrusions on the surgical device. The number and arrangement of protrusions can serve to uniquely identify the surgical device. In this way, the number and arrangement of buttons or other components that are engaged by the one or more protrusions on the surgical device can convey identification information about the surgical device. In another embodiment, the engagement features 40 can include a radio frequency identification (RFID) transceiver or optical scanner that is configured to read a unique device identifier (UDI) contained in either an RFID tag or bar code, respectively, on the surgical device. The identification information can include a type of the surgical device, a serial number of the surgical device, an angle at which the surgical device is configured to attach to the module 10, an age of the surgical device, an intended use of the surgical device, etc.

The identification information can be conveyed to the surgeon, for example to ensure that the module 10 has been securely attached to the correct surgical device. Where the module 10 is determined not to have been attached to the correct surgical device, the module 10 can alert the surgeon to the error, for example by displaying an error message on the display 50. In some embodiments, where the identification information includes an angular offset of a portion of the surgical device from the module 10 when the surgical device is attached to the module 10, the identification information can be used to calculate an absolute position and/or orientation of that portion of the surgical device. Additionally or alternatively, the identification information, e.g., a type of the surgical device, can cause the module 10 to detect and/or calculate different types of positional information. By way of non-limiting example, the module 10 can be configured to switch into the full detection mode when the engagement features 40 detect that the module 10 is connected to a surgical instrument that is intended to change position and orientation during surgery, and into the orientation detection mode when the engagement features 40 detect that the module 10 is connected to a surgical device, e.g., an implant, that is only or primarily intended to change orientation during the surgery. In still further embodiments, where the module 10 is in communication with an external display that provides a graphical depiction of the surgery in real-time based on positional information transmitted from the module 10, the external display can use the identification information to incorporate an illustration of the surgical device to which the module 10 is attached in the graphical depiction. The identification information can be stored along with positional information collected and/or calculated by the module 10 during surgery, e.g., to facilitate later reconstruction of the surgery.

The surgical electronic modules disclosed herein can generally be used to detect a position and/or orientation of a surgical device to which they are attached as well as changes in said position and/or orientation. Where the surgical device is also attached to a portion of a patient's anatomy, the surgical electronic module can be used to detect a position and/or orientation of that portion of the patient's anatomy as well as changes in said position and/or orientation. In an exemplary embodiment, two surgical electronic modules can be attached to two pedicle screws to detect an amount of correction in a patient's spinal curvature during a pedicle subtraction osteotomy.

Figure 4:
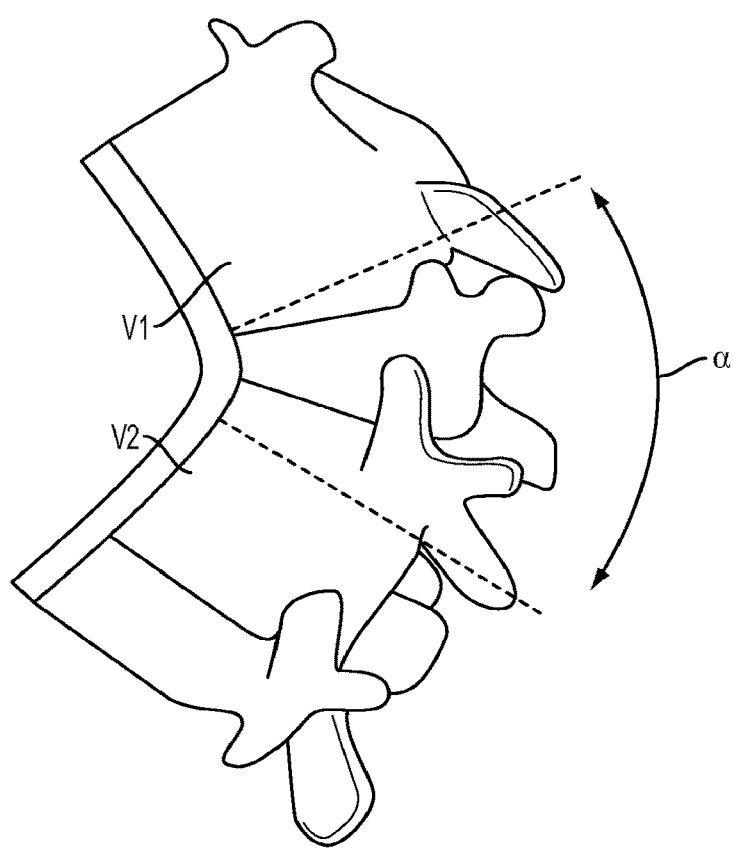
FIG. 4 is a perspective view of a spine of a patient with a spinal deformity.
Figure 5:
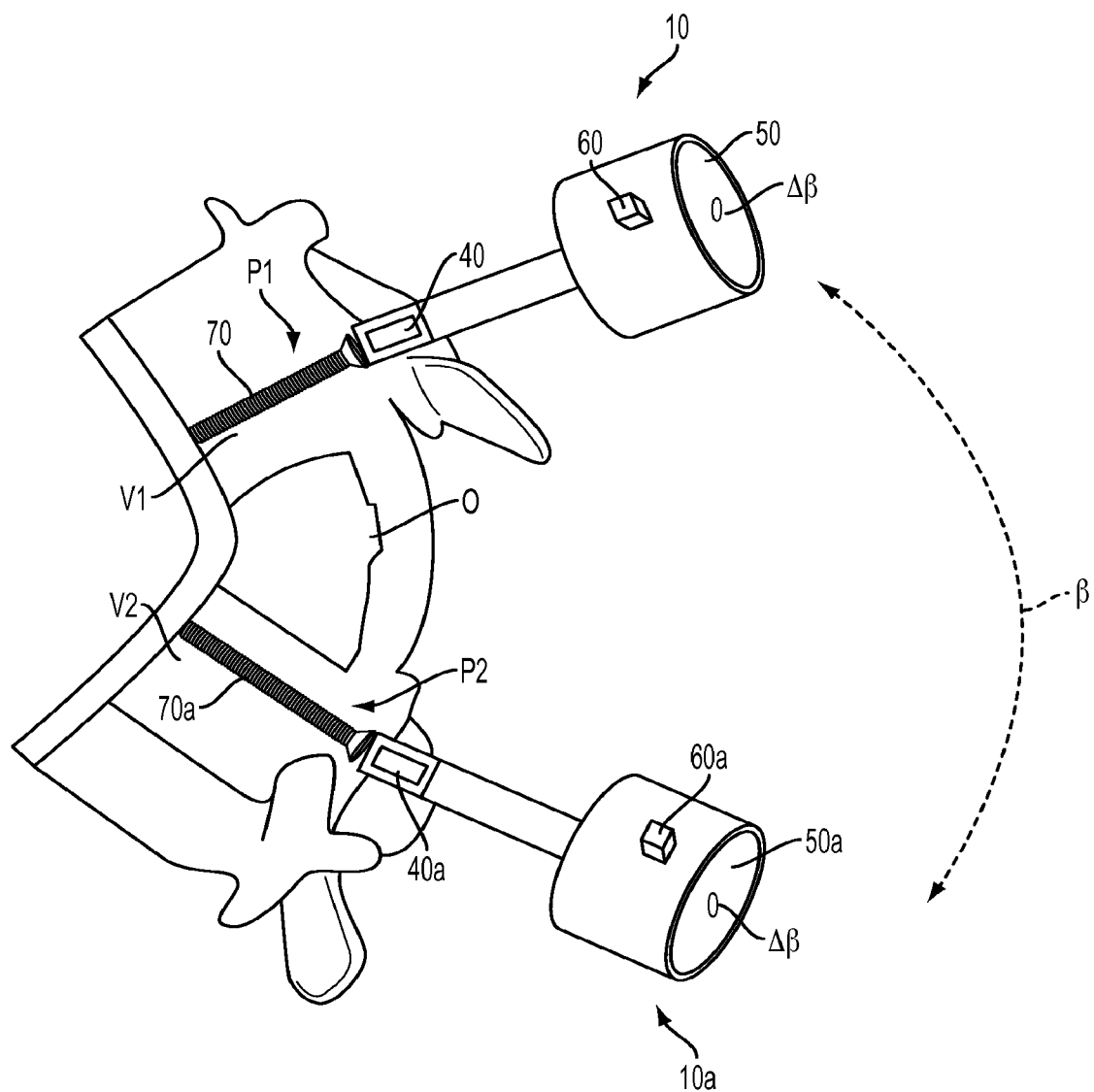
FIG. 5 is a perspective view of one step of an exemplary method for correcting spinal deformity using surgical electronic modules.
Figure 6:
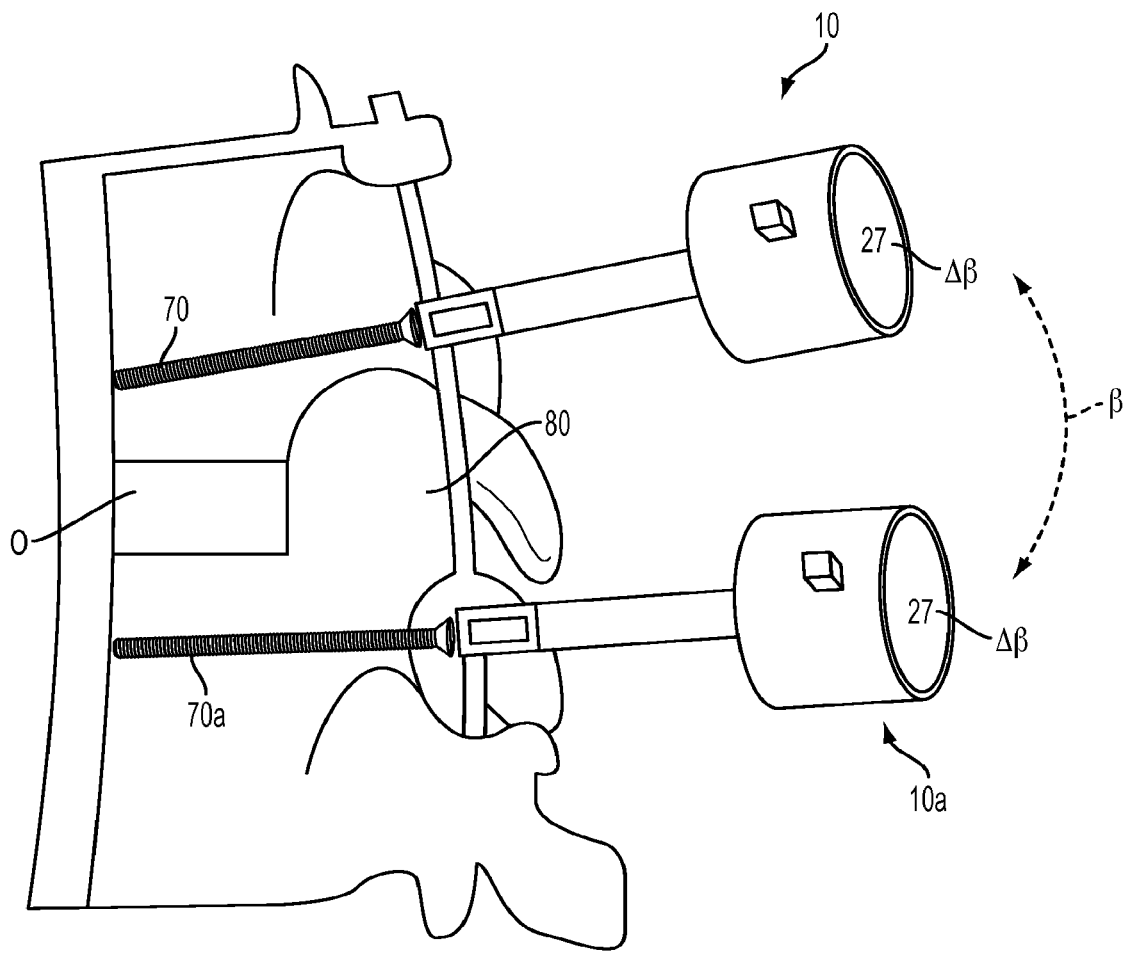
FIG. 6 is a perspective view of another step of the method of FIG. 5.

The steps of an exemplary pedicle subtraction osteotomy utilizing the module 10 and a second module 10a, which can be identical to the module 10, are illustrated in FIGS. 4-6. However, it will be appreciated by a person skilled in the art that any surgical electronic module as described herein can be used, either the same or different from one another, and that the modules 10, 10a can be used in a variety of surgical procedures that effect changes in anatomical position and/or orientation. Further, it will be appreciated that the calculations said to be performed by the modules 10, 10a can either be performed by both of the processors 22, 22a or by only one of the processors 22, 22a. Where the below-described calculations are performed by both of the processors 22, 22a, the modules 10, 10a can communicate the results of the calculations with one another to check for accuracy and can display an error message to the user when there is a mismatch. The calculations can also be performed by a remote base station configured to receive positional information from the modules 10, 10a.

As shown in FIG. 4, prior to the exemplary osteotomy procedure, the patient's lumbar spine includes a kyphotic deformity in which a first vertebra V1 is positioned at an angle α in the sagittal plane relative to a second vertebra V2. A purpose of the osteotomy procedure can be to reduce the angle α to a desired value, e.g., by removing a corresponding amount of bone from a vertebra disposed between the vertebrae V1, V2. The amount of angular correction can be determined based on pre-operative imaging and calculations. In some embodiments, prior to surgery, the modules 10, 10a can be calibrated to one another to thereby synchronize their coordinate systems. For example, the modules 10, 10a can be mechanically connected to one another via, e.g., the engagement features 40, 40a, and rotated through space as a pair until sufficient information has been gathered to synchronize their coordinate systems. An output signal can be provided to the user, for example a visual signal on the display 50, a vibration, and/or an audio signal, to indicate when synchronization has been completed. Such synchronization can facilitate automated error correction, e.g., for axial rotations, and/or can facilitate quantification of coronal plane changes.

First and second pedicle screws 70, 70a can be implanted into first and second pedicles P1 and P2 of first and second vertebrae V1 and V2, as shown in FIG. 5, according to customary surgical procedures. The first module 10 can be rigidly attached to the first pedicle screw 70 and the second module 10a can be rigidly attached to the second pedicle screw 70a via the engagement features 40, 40a of the first and second modules 10, 10a. The modules 10, 10a can be attached to the pedicle screws 70, 70a either before or after the pedicle screws are implanted. Through this series of connections, changes in the positions and/or orientations of the first and second modules 10, 10a can correspond to changes in positions and/or orientations of the first and second pedicle screws 70, 70a, respectively, and to changes in positions and/or orientations of the first and second pedicles P1, P2 to which the pedicle screws 70, 70a are attached.

Once the modules 10, 10a have been attached to the screws 70, 70a and the screws 70, 70a have been implanted in the pedicles P1, P2 in an initial position and/or orientation, the modules can be powered up and the zeroing buttons 60, 60a can be actuated to indicate to the modules 10, 10a that the modules 10, 10a are in the initial position and/or orientation. Thus, as shown in FIG. 5, the displays 50, 50a can each display "0" to indicate that the modules 10, 10a are oriented at an initial angle relative to one another. As the procedure is performed, the sensors 28, 28a of the modules 10, 10a can detect absolute azimuth and polar angles $\theta$, $\varphi$ of each of the modules 10, 10a with respect to the earth. The modules 10, 10a can communicate their absolute azimuth and polar angles $\theta$, $\varphi$ to one other via the communications interfaces 26, 26a. Given this information, the processors 22, 22a can then calculate a relative angle $\beta$ of the first module 10 with respect to the second module 10a in the sagittal plane (e.g., by subtracting the absolute angles measured by the modules). The relative angle $\beta$ at the initial position and/or orientation of the modules 10, 10a can be stored in the memories 24, 24a.

Angular correction of the spine along the sagittal plane can then be performed according to customary surgical procedures, which can include removal of bone between the first and second vertebrae V1, V2 at an osteotomy site O of a vertebra disposed between the vertebrae V1, V2. During the correction, the sensors 28, 28a can continually detect the absolute azimuth and polar angles $\theta$, $\varphi$ of the modules 10, 10a and the processors 22, 22a can continually calculate the relative angle $\beta$ based on the updated azimuth and polar angles $\theta$, $\varphi$. As the relative angle $\beta$ changes during the surgery, the processors 22, 22a can further calculate a change $\Delta\beta$ in the relative angle $\beta$ over a specified period of time. In the illustrated embodiment, where the modules 10, 10a were zeroed at the initial position and/or orientation, the change $\Delta\beta$ in the relative angle $\beta$ between the initial angle and the current angle (and thus the amount of correction achieved) can be displayed on the displays 50, 50a. In this way, the user can be provided with a real-time, quantitative measurement of angular correction throughout the surgery. When the desired angular correction has been achieved (FIG. 6), as indicated for example by the value of $\Delta\beta$ displayed on the displays 50, 50a, the patient's spine can be stabilized in the corrected position and/or orientation.

In some embodiments, the processors 22, 22a can further calculate derivatives of values detected by the sensors 28, 28a and/or calculated by the processors 22, 22a, such as $\beta$, $\theta$, and $\varphi$. By way of non-limiting example, the processors 22, 22a can calculate a first derivative of $\beta$, i.e., a rate of change $\Delta\beta/\Delta t$ in the relative angle $\beta$ over time, a second derivative of $\beta$, i.e., a relative acceleration $\Delta\beta/\Delta t^2$, and/or a third derivative of $\beta$, i.e., a relative jerk $\Delta\beta/\Delta t^3$ of the modules 10, 10a The rates of change $\Delta\beta/\Delta t$, $\Delta\theta/\Delta t$ and/or $\Delta\varphi/\Delta t$ can be useful for error checking, for example to indicate whether the patient has been accidentally moved during the procedure. For example, in embodiments where the processors 22, 22a calculate a rate of change $\Delta\theta/\Delta t$ for each of the modules 10, 10a, it can be assumed that the patient is moving when the rate of change $\Delta\theta/\Delta t$ of the first module 10 is equal to the rate of change $\Delta\theta/\Delta t$ of the second module 10a, since it is unlikely that the first and second modules 10, 10a would be moved at precisely the same rate as part of the surgical procedure. Thus, when the rate of change $\Delta\theta/\Delta t$ of the first module 10 is equal, or at least substantially equal, to the rate of change $\Delta\theta/\Delta t$ of the second module 10a, either or both modules 10, 10a can alert the surgeon to the patient's movement, for example by displaying an error message on the displays 50, 50a. Additionally or alternatively, to provide clinical feedback, the rates of change $\Delta\beta/\Delta t$, $\Delta\theta/\Delta t$ and/or $\Delta\varphi/\Delta t$ can be displayed, e.g., on the displays 50, 50a, and/or stored, e.g., in the memories 24, 24a. Information about the rates of change $\Delta\beta/\Delta t$, $\Delta\theta/\Delta t$ and/or $\Delta\varphi/\Delta t$ can be useful for clinicians because they provide a measure of how quickly an anatomical adjustment is made, which may correlate to patient outcomes.

In some embodiments, spinal fixation or stabilization hardware (e.g., screws and rods) can be coupled to a first side of the patient's spine before correction is performed without locking down the fixation hardware. The modules can be coupled to screws implanted in a second, contralateral side of the patient's spine. After the desired amount of correction is achieved, the fixation hardware in the first side of the patient's spine can be locked down to maintain the corrected angle. The modules can then be removed and a spinal fixation element 80 can be attached to the pedicle screws 70, 70a implanted in the second, contralateral side to complete the fixation. In other embodiments, spinal fixation or stabilization hardware can be coupled only to a single side of the patient's spine, e.g., a side on which the modules 10, 10a are attached. It will be appreciated that the modules 10, 10a can be removed from the pedicle screws 70, 70a either before or after a spinal fixation element or rod 80 is coupled to the pedicle screws.

The above-described method involves a single level osteotomy and first and second modules 10, 10a configured to measure a local correction, however it will be appreciated that more complex deformity correction can also be performed. For example, rotational deformities or angular deformities in any of the sagittal, axial, and/or coronal planes can be corrected and the degree of correction monitored using the modules disclosed herein. By way of further example, several modules (e.g., three, four, five, six, seven, eight, or more) can be coupled to corresponding vertebrae to provide correction measurements for a spinal segment (e.g., a lumbar region, a thoracic region, a cervical region, etc.) or for an entire spine (e.g., from skull to tailbone). Measurement data associated with such procedures can be communicated to an external display to give the surgeon a graphical depiction of overall spinal correction.

Although not shown, additional information can be displayed on the displays 50, 50a and/or on an external display in communication with the modules 10, 10a. The information displayed on the display 50 can be selected by a user before the procedure, can be impacted by the surgical device to which the module 10 is attached, and/or can be preconfigured as part of the factory settings of the module 10. By way of non-limiting example, the modules 10, 10a can convey positive and/or negative feedback to the surgeon during surgery. For example, the displays 50, 50a can convey an error message to the user when the change $\Delta\beta$ in the relative angle $\beta$ exceeds the desired angular correction, when the engagement features 40, 40a detect that they are not attached to the correct surgical device, and/or when engagement between the engagement features 40, 40a and the pedicle screws 70, 70a has been lost or weakened. In some embodiments, where the processors 22, 22a are configured to calculate the rate of change $\Delta\beta/\Delta t$ in the relative angle $\beta$, the displays 50, 50a can convey an error message to the user when the rate exceeds a predetermined speed limit. In still further embodiments, should the patient be rotated in the axial plane during the surgery, for example due to a table rotation or rolling over of the patient, one or both of the modules 10, 10a can detect the change and can be configured to alert the surgeon via an error message on the displays 50, 50a, which may include an instruction to recalibrate. In case of a need to recalibrate, the modules 10, 10a can be detached from the screws 70, 70a and can be attached to one another to repeat the calibration procedure described above.

Information detected and/or calculated by the modules 10, 10a during the procedure can be collected and stored for later use. The information can be stored locally in the memories 24, 24a and/or can be transmitted via the communications interfaces 26, 26a to one or more external base stations. The stored information can be used at a later time for various purposes, for example to create a reproduction of the surgery, for clinical improvement, research, and/or ethnography.

Figure 7:
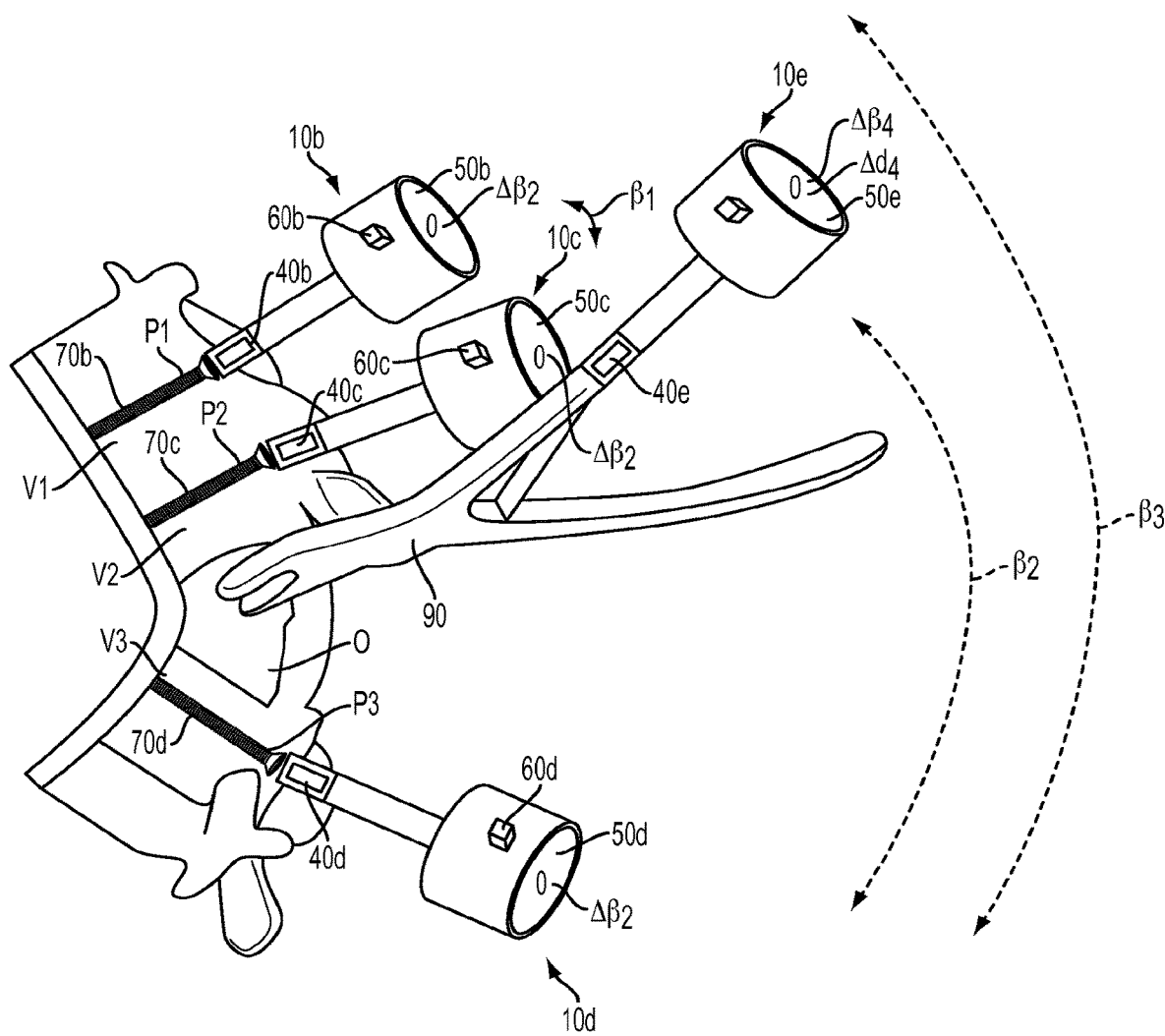
FIG. 7 is a perspective view of one step of another exemplary method for correcting spinal deformity using surgical electronic modules.
Figure 8:
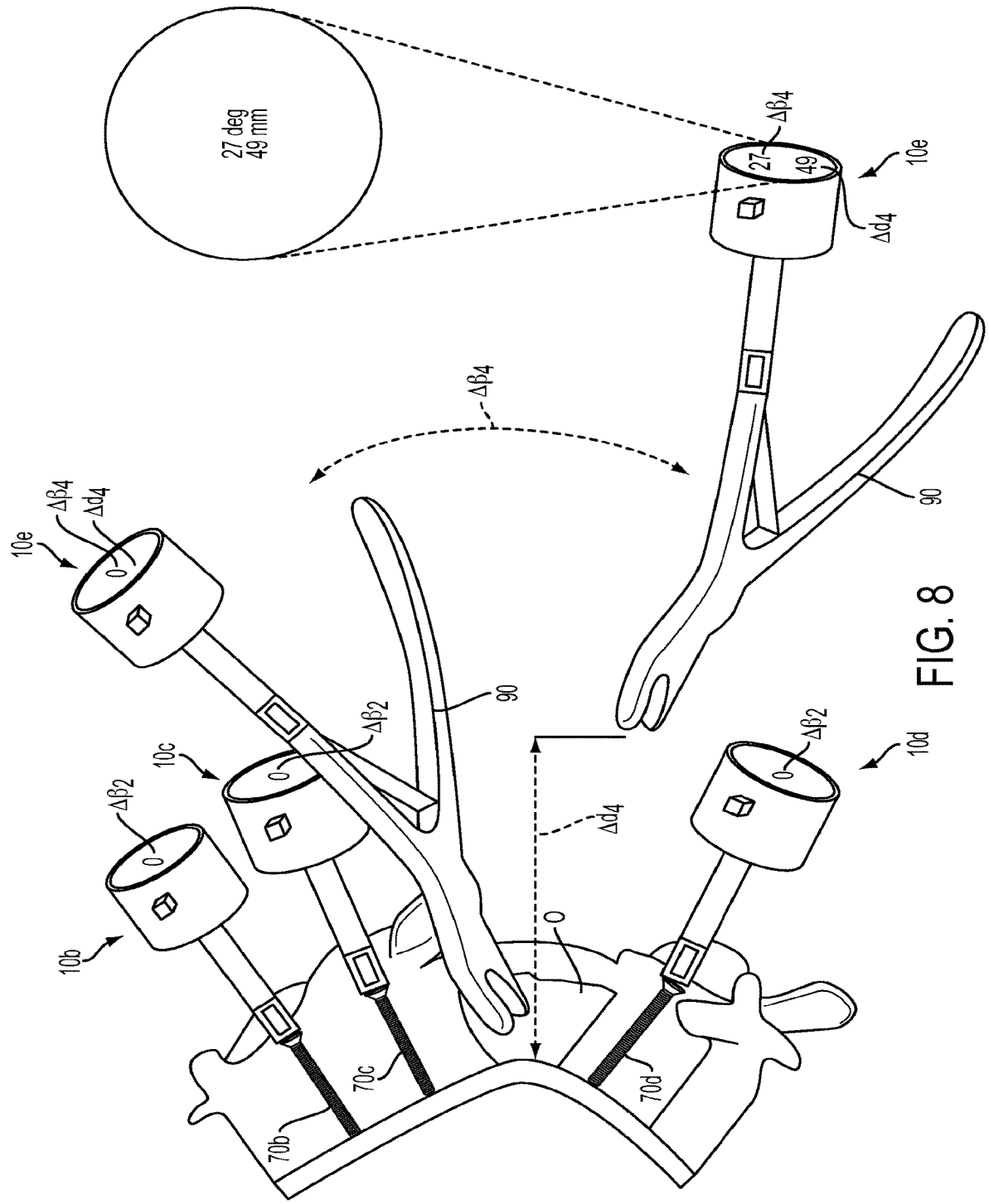
FIG. 8 is a perspective view of another step of the method of FIG. 7.

Another exemplary pedicle subtraction osteotomy using one or more surgical electronic modules as described herein is illustrated in FIGS. 7-8. The procedure according to this method involves the use of four surgical electronic modules 10b, 10c, 10d, 10e, which can detect, calculate, store, and/or transmit information in a similar manner to the modules 10, 10a described above during the exemplary pedicle subtraction osteotomy of FIGS. 4-6. It will be appreciated by a person skilled in the art that any surgical electronic module as described herein can be used, either the same or different from one another, and that the modules 10b, 10c, 10d, 10e can be used in a variety of surgical procedures that effect changes in anatomical position and/or orientation.

Similarly to the procedure described with reference to FIGS. 4-6, a desired angular correction of the spine can be determined prior to the surgery. The modules 10b, 10c, 10d, 10e can be calibrated by freely rotating mated pairs of the modules 10b, 10c, 10d, 10e until enough positional information has been acquired to synchronize their coordinate systems. For example, the module 10b can be attached to each of the other modules 10c, 10d, 10e, and synchronized with each of the other modules 10c, 10d, 10e to ensure that all of the modules 10b, 10c, 10d, 10e are synchronized to each other.

The first three modules 10b, 10c, 10d can be rigidly attached to three pedicle screws 70b, 70c, and 70d, while the fourth module 10d can be rigidly attached to a surgical cutting instrument such as a rongeur 90. The engagement features 40b, 40c, 40d, 40e can detect an identity of the device to which the modules 10b, 10c, 10d, 10e are attached, such that the first three modules 10b, 10c, 10d can detect that they are each attached to a pedicle screw and the fourth module 10e can detect that it is attached to a rongeur. Based on this information, the first three modules 10b, 10c, 10d can switch into the orientation detection mode in which only orientation information is displayed to the user, and the fourth module 10e can switch into the full detection mode in which orientation and position information is displayed. Further, as explained in detail below, the processors 22b, 22c, 22d of the first three modules 10b, 10c, 10d can be configured to calculate different positional information from the processor 22e of the fourth module 10e. It will be appreciated by a person skilled in the art, however, that the procedure can be performed utilizing only three modules, two of which are attached to two pedicle screws and the third of which is attached to a surgical cutting instrument.

The pedicle screws 70b, 70c, 70d can be implanted into pedicles P1, P2, and P3 on vertebrae V1, V2, and V3, either before or after the modules 10b, 10c, 10d are attached thereto. At least one of the pedicle screws 70b, 70c, 70d can be implanted on an opposite side of an intended osteotomy site O from at least one of the other pedicle screws 70b, 70c, 70d. Similarly to the modules 10, 10a used in the exemplary procedure of FIGS. 4-6, an initial position and/or orientation of the modules 10b, 10c, 10d with respect to one another can be set by actuating the zeroing buttons 60b, 60c, 60d. Thus, as shown in FIG. 7, the displays 50b, 50c, 50d can each display "0" to indicate that the modules 10b, 10c, 10d are oriented at an initial angle relative to one another. Angular correction of the spine along the sagittal plane can then be performed according to customary surgical procedures, which can include removal of bone from a vertebra disposed between the second and third vertebrae V2, V3 by the rongeur 90. During the procedure, the sensors 22b, 22c, 22d can continually detect absolute azimuth and polar angles $\theta$, $\varphi$ of each of the modules 10b, 10c, 10d. The modules 10b, 10c, 10d can communicate their absolute azimuth and polar angles $\theta$, $\varphi$ with each other (e.g., via Bluetooth or other wired or wireless communication) to thereby allow for the processors 22b, 22c, 22d to calculate a relative angle $\beta_1$ of the first module 10b with respect to the second module 10c, a relative angle $\beta_2$ of the second module 10c with respect to the third module 10d, and a relative angle $\beta_3$ of the first module 10b with respect to the third module 10d. Further, the modules 10b, 10c, 10d can calculate changes $\Delta\beta_1$, $\Delta\beta_2$, $\Delta\beta_3$ in the relative angles $\beta_1$, $\beta_2$, $\beta_3$ throughout the procedure, rates of changes $\Delta\beta_1/\Delta t$, $\Delta\beta_2/\Delta t$, $\Delta\beta_3/\Delta r$ and/or rates of changes $\Delta\theta/\Delta t$, $\Delta\varphi/\Delta t$ in the azimuth and polar angles $\theta$, $\varphi$ of each of the modules 10b, 10c, 10d.

Because the relative angle $\beta_1$ of the modules 10b, 10c with respect to one another does not change throughout the procedure since the modules 10b, 10c are on the same side of the osteotomy site O, the modules 10b, 10c, 10d can be configured to display only $\Delta\beta_2$. The displays 50b, 50c, 50d can be configured not to display the change $\Delta\beta_1$ since it will remain substantially equal to zero throughout the procedure, and not to display the change $\Delta\beta_3$ because $\Delta\beta_2$ and $\Delta\beta_3$ will remain substantially equal to one another throughout the procedure. Of course, it will be appreciated by a person of skill in the art that the modules 10b, 10c, 10d could display either $\Delta\beta_2$ and $\Delta\beta_3$, since they are substantially equal to one another, and $\Delta\beta_2$ has been chosen solely for purposes of illustration. Also, if at any point during the surgery, $\Delta\beta_1$ ceases to be substantially equal to zero and/or $\Delta\beta_2$ and $\Delta\beta_3$ cease to be substantially equal to one another, all three relative angular changes $\Delta\beta_1$, $\Delta\beta_2$, $\Delta\beta_3$ can be displayed on the displays 50b, 50c, 50d. Any of these values can be displayed on an external display alternatively or in addition.

The module 10e can be attached to the rongeur 90 via engagement features 40e on the module 10e at any point during the surgery to help the surgeon remove a desired amount of bone from a desired location. Like the modules 10b, 10c, 10d, the module 10e can be "zeroed" by user actuation of the zeroing button 60e when the module 10e is placed in an initial position and/or orientation, e.g., when the rongeur 90 to which the module 10e is coupled is inserted at a desired cutting angle and at a maximum desired cutting depth into the patient's body. Thus, as shown in FIG. 7, the module 10e can display two zeros, one indicating an initial angle and one indicating an initial distance. Preferably, the module 10e is zeroed before any angular correction in the patient's spine has been achieved and/or at the same time that the other modules 10b, 10c, 10d are zeroed.

Because the module 10e is able to detect that it is attached to a surgical instrument, e.g., the rongeur 90, as opposed to a surgical implant, e.g., the pedicle screws 70b, 70c, 70d, it can be configured to calculate and/or display different positional information than the modules 10b, 10c, 10d. This information can supplement the information displayed by the modules 10b, 10c, 10d to confirm that a desired angular correction has been achieved. In particular, whereas the modules 10b, 10c, 10d are configured to calculate and/or display changes in positional information with respect to one another, the module 10e can be configured to calculate and/or display changes in its own positional information throughout the surgery. Further, whereas the modules 10b, 10c, 10d are configured to calculate and/or display changes in their relative orientations, the module 10e can be configured to calculate and/or display changes in both orientation and position.

To perform these calculations, the module 10e can continually detect absolute azimuth and polar angles $\theta$, $\varphi$ of the module 10e with the sensor 28e, calculate an absolute angle $\beta_4$ of the module 10e in the sagittal plane with the processor 22e, and store the absolute angle $\beta_4$ for any given time in the memory 24e. Similarly, the sensor 28e can continually detect an absolute position (e.g., including a distance $d_4$ of the module 10e relative to a starting position) via triangulation, time-of-flight, or other positioning algorithms using ultrasonic, electromagnetic, and/or infrared location signals sent by each of the modules 10b, 10c, 10d, 10e and communicated therebetween. It will be appreciated by a person skilled in the art that, where at least three modules are used, unique position information can be created through location signals sent out by each of the modules and communication among all of the modules of the information received from the signals while the modules 10b, 10c, 10d are stationary, e.g., before they are moved together as part of reduction procedure. It will further be appreciated by a person skilled in the art that the position of the rongeur 90 can be determined through communication between the module 10e and other surgical electronic modules positioned in the operating room. As the position and/or orientation of the rongeur 90 changes during surgery, the processor 22e can calculate and the display 50e can display a change $\Delta\beta_4$ in the angle $\beta_4$ and/or a change $\Delta d_4$ in the distance $d_4$ of the module 10e—and therefore of the rongeur 90—in the sagittal plane. For example, as shown in FIG. 8, the display 50e can indicate that the rongeur 90 has moved by a distance of 49 mm and by an angle of 27 degrees from the initial position and orientation. In this way, the surgeon can know when the rongeur 90 has completed a desired motion to thereby remove a desired amount of bone. In some embodiments, the module 10e can be configured to alert the surgeon when the rongeur 90 is moved outside of or beyond a surgical plane, e.g., beyond a desired angle and/or distance, for example by displaying an error message on the display 50 and/or providing an audio signal or vibration. For example, the surgeon can be warned when the distal end of the rongeur is approaching or has exceeded a predetermined maximum insertion depth in the anterior direction (e.g., when the axial displacement of the rongeur relative to the starting position approaches zero or becomes negative).

Similarly to the exemplary pedicle subtraction osteotomy of FIGS. 4-6, when the desired angular correction of the spine in the sagittal plane has been achieved, the change $\Delta\beta_2$ in the relative angle $\beta_2$ displayed on the displays 50b, 50c, 50d will be equal to the desired angular correction. The patient's spine can then be stabilized in the corrected position via a spinal fixation element 80 that can be attached to the implanted pedicle screws 70b, 70c, 70d. The modules 10b, 10c, 10d can be removed from the pedicle screws 70b, 70c, 70d and the module 10e can be removed from the rongeur 90 either before or after fixation with the spinal fixation element 80.

It will be appreciated by a person skilled in the art that a greater number of modules can enhance the accuracy of the procedure by providing for a greater amount of positional information. For example, using more modules can provide positional information to a greater degree of precision and/or specificity, e.g., with more significant digits, which can be displayed to the surgeon. As each module is added in the procedure, the number of significant digits displayed to the surgeon can increase, thereby providing a measure of the increase in accuracy added by each additional module to the surgeon. Additionally or alternatively, using a greater number of modules can enable the modules to detect and/or calculate their positions and/or orientations in more dimensions. The positions, orientations and/or changes in the positions and/or orientations of the modules can be displayed to the user for each plane in which information is acquired. However, it will also be appreciated by a person of skill in the art that a position and/or an orientation of the module in certain planes need not be calculated since it can be assumed that the patient will not move in certain planes.

It will further be appreciated by a person skilled in the art that the devices and methods described herein can be particularly useful for robotic assisted surgery. For example, one or more surgical electronic modules as described herein can transmit positional information to a robotic manipulator, which can manipulate the one or more modules until they have reached a desired final position that has been input to the manipulator.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A surgical method, comprising:
    attaching a first sensor to a first vertebra of a spine of a patient;
    attaching a second sensor to a second vertebra of the spine of the patient;
    detecting and transmitting position information using a first processor of the first sensor and a second processor of the second sensor in real-time;
    performing an angular correction of the spine along one or more of the axial, coronal, or the sagittal planes to achieve segmental or global plane alignment;
    using a third processor, continually calculating an angular orientation of the first and second sensors throughout the angular correction; and
    displaying a real-time, quantitative measurement of angular correction of the spine throughout the angular correction.

2. The method of claim 1, further comprising measuring segmental or global plane alignment of the spine.

3. The method of claim 1, wherein detecting position information is performed without intraoperative imaging.

4. The method of claim 1, further comprising preoperatively determining a desired spinal correction associated with the patient, the desired spinal correction including a desired correction angle.

5. The method of claim 4, further comprising stabilizing the spine when angular correction of the spine aligns with the desired correction angle.

6. The method of claim 1, further comprising one or more of the first sensor or the second sensor communicating its position to the other sensor.

7. The method of claim 6, further comprising, using the third processor, calculating a relative angle of the first sensor with respect to the second sensor in the sagittal plane.

8. The method of claim 7, further comprising attaching an additional sensor to one or more of a third vertebra or a surgical instrument, the additional sensor calculating different positional information from the first sensor and the second sensor.

9. The method of claim 8, further comprising displaying a first set of information on the first and second sensors while displaying a second set of information on the third sensor.

10. The method of claim 9, wherein the first set of information comprises orientation information and the second set of information comprises orientation and position information.

11. The method of claim 1, wherein the angular correction is performed along the sagittal plane.

12. The method of claim 1, wherein displaying the real-time, quantitative measurement of angular correction comprises a color-coded visual indication.

13. A surgical method comprising:
attaching a first sensor to a first vertebra;
attaching a second sensor to a second vertebra;
detecting and transmitting position information using a first processor of the first sensor and a second processor of the second sensor in real-time;
adjusting a position of the first vertebra with respect to the second vertebra; and
using a third processor, determining and graphically displaying an angle related to relative positions of the first vertebra and the second vertebra based on real-time quantitative intraoperative assessment of data from the first sensor and the second sensor.

14. The method of claim 13, wherein determining the surgically-corrected angle further comprises calculating the surgically-corrected angle based on data from the first sensor and the second sensor.

15. The method of claim 14, wherein the surgically-corrected angle is calculated continually throughout changes in orientation of the surgically-corrected angle.

16. The method of claim 13, wherein the first sensor and the second sensor are configured to graphically display the surgically-corrected angle.

17. The method of claim 13, further comprising preoperatively determining a desired spinal correction associated with a patient, the desired spinal correction including a desired correction angle.

18. The method of claim 17, further comprising using the third processor, providing feedback regarding the surgically-corrected angle relative to the desired correction angle.

19. The method of claim 18, wherein the feedback includes a color-coded visual indication.

20. A surgical method, comprising:
attaching a first sensor of a plurality of sensors to a first vertebra of a spine of a patient;
attaching a second sensor of the plurality of sensors to a second vertebra of the spine of the patient;
monitoring positions of each of the first vertebra and the second vertebra in real-time using the plurality of sensors coupled thereto;
performing angular correction of the spine along one or more of the axial, coronal, or the sagittal planes to achieve segmental or global plane alignment;
using a processor, continually detecting an angular orientation of the first and second sensors throughout the angular correction; and
displaying a real-time, quantitative measurement of angular correction of the spine throughout the angular correction,
wherein displaying the real-time, quantitative measurement of angular correction comprises a color-coded visual indication.

* * * * *